United States Patent
Brauer

(10) Patent No.: US 6,187,207 B1
(45) Date of Patent: Feb. 13, 2001

(54) METHOD AND DEVICE FOR CHECKING PROPER REPLACEMENT OF A USED FILTER IN A DEVICE FOR EXTRACORPOREAL TREATMENT OF BLOOD

(75) Inventor: Helge Brauer, Gochsheim (DE)

(73) Assignee: Fresenius Medical Care Deutschland GmbH, Bad Homburg (DE)

( * ) Notice: Under 35 U.S.C. 154(b), the term of this patent shall be extended for 0 days.

(21) Appl. No.: 09/356,541

(22) Filed: Jul. 19, 1999

(30) Foreign Application Priority Data

Jul. 18, 1998 (DE) ............................... 198 32 451

(51) Int. Cl.[7] .................................................. B01D 61/30
(52) U.S. Cl. .................................. 210/739; 73/38; 73/40; 210/90; 210/646; 210/741
(58) Field of Search ............................... 210/85, 90, 646, 210/739, 741; 73/38, 40; 604/4.01, 5.01

(56) References Cited

U.S. PATENT DOCUMENTS 5,674,404 * 10/1997 Kenley et al. ..................... 210/741

5,808,181 * 9/1998 Wamsiedler et al. ................ 210/646

FOREIGN PATENT DOCUMENTS

| 34 42 744 | 6/1986 | (DE) . |
| 34 44 671 | 6/1986 | (DE) . |
| 34 48 262 | 6/1990 | (DE) . |
| 39 23 078 | 9/1990 | (DE) . |
| 0 763 376 | 3/1997 | (EP) . |

* cited by examiner

Primary Examiner—Joseph W. Drodge
(74) Attorney, Agent, or Firm—Kenyon & Kenyon

(57) ABSTRACT

A method and a device for verifying the proper replacement of a used filter that is divided into two chambers by a membrane in a device for extracorporeal treatment of blood. The verification of whether the filter has been properly replaced with a new filter is performed by a pressure retaining test, which determines whether the membrane of the filter is permeable to gas. In the event the membrane is permeable to gas, it is concluded that the used filter has been replaced by a new filter.

13 Claims, 1 Drawing Sheet

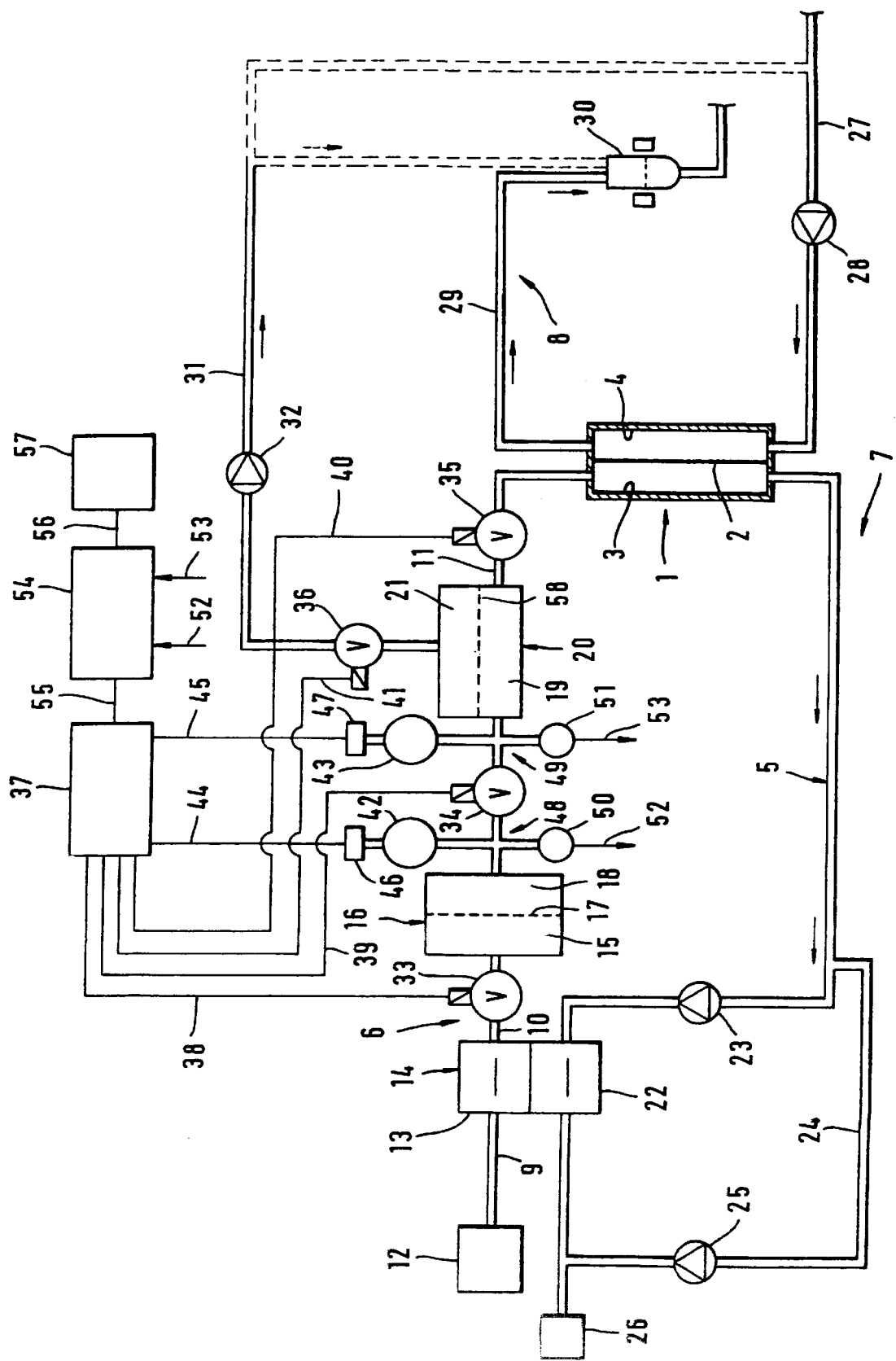

METHOD AND DEVICE FOR CHECKING PROPER REPLACEMENT OF A USED FILTER IN A DEVICE FOR EXTRACORPOREAL TREATMENT OF BLOOD

BACKGROUND OF THE INVENTION

The present invention relates to a method of verifying proper replacement of a used filter that is divided by a membrane into two chambers and that is arranged in the fluid system of a device for extracorporeal treatment of blood. In addition, the present invention relates to a device for extracorporeal treatment of blood with a fluid system containing at least one filter divided by a membrane into a first and a second chamber, so that proper filter replacement is verifiable.

DESCRIPTION OF RELATED ART

To remove substances usually eliminated with the urine and for removal of fluids, various methods of extracorporeal treatment or purification of blood are used to treat chronic renal failure. In hemodialysis, a patient's blood is purified outside the patient's body in an artificial kidney known as a dialyzer. The dialyzer has a blood chamber and a dialysis fluid chamber separated by a semipermeable membrane. During the treatment, the patient's blood flows through the blood chamber on one side of the membrane. To effectively purify blood of substances usually eliminated with the urine, fresh dialysis fluid flows continuously through the dialysis fluid chamber.

Diffuse mass transport is the predominant mechanism in hemodialysis (HD), while convective mass transport through the membrane dominates in hemofiltration (HF). Hemodiafiltration (HDF) is a combination of the two methods. In hemo(dia)filtration, a portion of the serum removed through the membrane is replaced by a sterile replacement fluid added to the extracorporeal blood circuit, either upstream from the dialyzer (predilution) or downstream from the dialyzer (postdilution).

In current devices for hemo(dia)filtration the dialysis fluid is prepared online from fresh water and an electrolyte concentrate, and the replacement fluid is prepared online from the dialysis fluid. To ensure that the dialysis fluid and replacement fluid prepared online are sterile and free of pyrogens, the fluids are passed through filters arranged in the fluid system of the hemo(dia)filtration machine. These filters are divided into two chambers by a microbe-retaining membrane. Such a device with two filters arranged in the dialysis fluid system is known from German Patent 34 44 671 C2.

German Patent 34 48 262 C2 describes a method of verifying that the filters of the hemo(dia)filtration machine known from German Patent 34 44 671 C2 are leakproof. The filter integrity test is performed using a pressure retaining test, with a partial vacuum being established in one of the two chambers of the filter. The pressure retaining test is based on the fact that when the membrane of the filter is wetted with a fluid, it is essentially impermeable to gases. An increase in pressure in the chamber can be detected during the pressure retaining test only when there is a defect.

German Patent 34 42 744 A1 describes a membrane integrity test for a used dialyzer, where the chambers of the dialyzer are filled with air, and equalization of pressure across the wetted membrane is observed.

Manufacturers of known sterile filters for hemo(dia)filtration machines suggest the replacement of filters at certain intervals, for reasons of safety. There are known hemo(dia)filtration machines which notify the user automatically when it is necessary to change the filter. To increase safety, the known hemo(dia)filtration machines also provide for manual confirmation of replacement of the filter by the user. However, this safety device cannot prevent the user from simply confirming that the filter has been replaced, without having actually replaced the filter.

SUMMARY OF THE INVENTION

The present invention is directed to a device and method for verifying proper replacement of a used filter in the fluid system of a machine for extracorporeal treatment of blood that substantially obviates one or more of the problems due to limitations and disadvantages of the related art.

Additional features and advantages of the invention will be set forth in the description which follows, and in part will be apparent from the description, or may be learned by practice of the invention. The objectives and other advantages of the invention will be realized and attained by the apparatus and method particularly pointed out in the written description and claims hereof, as well as the appended drawing.

To achieve these and other advantages and in accordance with the purpose of the invention, as embodied and broadly described, the invention is a method for determining if a filter in the fluid system of a device for extracorporeal treatment of blood has been replaced with a new filter, that includes measuring whether a membrane of the filter that divides the filter into a first and a second chamber is permeable to gas and, in the event the membrane is permeable to gas, concluding that the filter has been replaced.

In another aspect, the invention is a device for extracorporeal treatment of blood, that includes at least one filter divided by a membrane into a first chamber and a second chamber, disposed along a fluid system of the device, and means for measuring a gas permeability of the membrane of the at least one filter. The device also includes means for determining whether the at least one filter has been replaced by a corresponding new filter, based on the gas permeability of the membrane.

One object of the present invention is to provide a method that will make it possible to ascertain with a high degree of certainty whether a used filter has been replaced by a new filter. In addition, another object of the present invention is to provide a device for extracorporeal treatment of blood that includes a device for verifying with a high degree of certainty whether proper replacement of the filter was carried out.

It is assumed in the present invention that the membrane of a new filter is dry, while the membrane of a used filter is wetted with fluid. A pressure retaining test is performed to verify the proper replacement of the filter. Verification is undertaken to determine whether the membrane of the filter is permeable to gas. If the membrane is impermeable to gas, it is concluded that the membrane is wetted with fluid, and that the filter installed is a used filter.

By using the pressure retaining test, proper replacement of all filters arranged in the fluid system of the machine for extracorporeal treatment of blood can be tested. This includes the filters for supplying sterile dialysis fluid and replacement fluid as well as the dialyzer filter itself.

The gas permeability of the membrane of the filter can be verified by a vacuum test or an excess pressure test. Preferably, a section of the fluid system including the first chamber of the filter and another section including the second chamber of the filter are isolated. Gas is then directed into one of the two sections to build up an excess pressure, which is monitored. The other section of the fluid system is then opened again, and if there is a pressure drop in the isolated section, it is deduced that the filter has been properly replaced. With this system it is also possible to verify whether an excess pressure can be built up and maintained in the isolated section of the fluid system that includes one of the two chambers. If that is the case, the filter is a used filter whose membrane is wetted with fluid.

The pressure drop per unit of time, or rate of pressure drop, is preferably compared to a predetermined limit value. If this limit value is exceeded, it can be deduced that the filter has been properly replaced. This ensures that it will be possible to differentiate between a pressure drop due to the fact that the membrane of the filter is not wetted with fluid, and the more minor pressure drop also detected with a membrane wetted with fluid over a long period of time.

To build up an excess pressure, it is preferable to direct atmospheric air into one of the two sections of the fluid system, where the excess pressure can be established with an air pump. To prevent microorganisms from entering the fluid system, the air is preferably passed through a hydrophobic filter.

When the used filter has not been replaced by a new filter, an optical and/or an acoustic alarm can be advantageously displayed or sounded. However, it is also possible in this case to prevent further operation of the extracorporeal blood treatment machine, so that treatment cannot be continued unless the used filter is replaced.

It is to be understood that both the foregoing general description and the following detailed description are exemplary and explanatory and are intended to provide further explanation of the invention as claimed.

BRIEF DESCRIPTION OF THE DRAWING

The accompanying drawing, which is incorporated in and constitutes a part of this specification, illustrates an embodiment of the invention and, together with the description, serves to explain the objects, advantages, and principles of the invention.

The drawing shows a schematic diagram of a hemo(dia) filtration machine whose dialysis fluid system contains two filters

DETAILED DESCRIPTION OF THE PREFERRED EMBODIMENTS

The hemo(dia)filtration machine shown in the drawing has a dialyzer 1 divided by a membrane 2 into a first chamber 3 through which dialysis fluid flows and a second chamber 4 through which blood flows. The first chamber 3 is connected to a dialysis fluid path 5 of the dialysis fluid system of the extracorporeal blood treatment machine, which has an inlet line 6 and an outlet line 7. The second chamber 4 is connected to a blood path 8.

Inlet line 6 of dialysis fluid path 5 includes a first inlet line section 9, a second inlet line section 10 and a third inlet line section 11, and connects a dialysis fluid source 12 to the first chamber 3 of dialyzer 1. The first inlet line section 9 leads from dialysis fluid source 12 to a first balancing chamber 13 of a balancing device 14 having two balancing chambers. First balancing chamber 13 of balancing device 14 is connected by second inlet line section 10 to the inlet of a first chamber 15 of a first sterile filter 16, which is divided by a microorganism-retaining hydrophilic membrane 17 into a first chamber 15 and a second chamber 18. To the third inlet line section 11 is connected the first chamber 19 of a second sterile filter 20, which is also divided into a first chamber 19 and a second chamber 21 by a microorganism-retaining hydrophilic membrane 58.

Outlet line 7 leads from the outlet of the first chamber 3 of dialyzer 1 to the second balancing chamber 22 of balancing device 14. A dialysis fluid pump 23 is connected to the outlet line. An ultrafiltrate line 24 branches off from outlet line 7, upstream from dialysis fluid pump 23, and is connected to an ultrafiltration pump 25 for removing dialysis fluid. Ultrafiltrate line 24 leads to a drain 26 which is also connected to the outlet of the second balancing chamber 22 of balancing device 14.

Blood path 8 has a blood inlet line 27 coming from the patient's blood vessels and connected to the inlet of the second chamber 4 of dialyzer 1. A pump 28 is connected to blood inlet line 27. The outlet of the second chamber 4 of dialyzer 1 leads through the first section of a blood outlet line 29 to a drip chamber 30 from which blood is carried to the patient over the second section of blood outlet line 29.

The dialysis fluid system also has a replacement fluid line 31 that branches from the second chamber 21 of the second sterile filter 20 and may optionally be connected to blood inlet line 27 (predilution) or to drip chamber 30 (postdilution). The two connecting branches are indicated with dotted lines. A replacement fluid pump 32 is connected to replacement fluid line 31.

The hemo(dia)filtration machine according to the invention has a device for verifying that two sterile filters 16, 20 have been properly replaced. The device for verifying proper filter replacement includes a first shut-off element 33 connected to the second inlet line section 10, a second shut-off element 34 connected to the third inlet line section 11 upstream from the second sterile filter 20, a third shut-off element 35 connected to the third inlet line section 11 downstream from the second sterile filter 20, and a fourth shut-off element 36 connected to the replacement fluid line 31. The shut-off elements are electromagnetically operated valves driven by a central control unit 37 over control lines 38, 39, 40, 41.

Electric air pumps 42, 43 are connected by control lines 44, 45 to central control unit 37, and are also connected to the third inlet line section 11 upstream and downstream from the second shut-off element 34. Air pumps 42, 43 pump air from the atmosphere through a hydrophobic sterile filter 46, 47 to build up an excess pressure in the isolatable line sections 48, 49 of the dialysis fluid system. In addition, pressure gauges 50, 51 are connected to the third inlet line section 11 upstream and downstream from the second shut-off element 34 for monitoring the pressure in the isolatable line sections.

Pressure gauges 50, 51 are connected by control lines 52, 53 to an analyzing unit 54, which is in turn connected by a data line 55 to central control unit 37. An acoustic and/or optical alarm device 57 is connected to analyzing unit 54 by a signal line 56.

The method according to the present invention for verifying whether the filter has been properly replaced will now be described in detail. As a first step, central control unit 37 closes shut-off elements 33 through 36. Then control unit 37 starts operation of air pumps 42, 43, so that an excess pressure is built up in isolated line sections 48, 49 of the fluid system of the hemo(dia)filtration machine. The pressure is monitored by pressure gauges 50, 51. After a predetermined excess pressure has built up in the isolated line sections, the control unit stops the air pumps and opens shut-off elements 33 and 36. Analyzing unit 54 compares the pressure measured by pressure gauges 50, 51 to a predetermined limit value. The appropriate predetermined limit value can be determined, for example, for each type of filter used.

If the pressure in the line sections of the fluid system including the second chamber 18 of the first sterile filter 16 and the first chamber 19 of the second sterile filter 20 does not drop below a predetermined limit value within a predetermined period of time, analyzing unit 54 triggers the alarm device 57 to deliver an acoustic and/or optical alarm. In a preferred embodiment according to the invention, the measurement time can be about ten seconds, and the predetermined limit can correspond to approximately half the pressure originally built up in the isolated line branches.

In another embodiment according to the invention, a common air pump and a common pressure gauge may also be provided for both the isolated line sections, without using two independent air pumps and pressure gauges.

It will be apparent to those skilled in the art that various modifications and variations can be made in the structure and methodology of the present invention, without departing from the spirit or scope of the invention. Thus, it is intended that the present invention cover the modifications and variations of this invention provided they come within the scope of the appended claims and their equivalents.

What is claimed is:

1. A method for determining if a filter in the fluid system of a device for extracorporeal treatment of blood has been replaced with a new filter, comprising:

measuring whether a membrane of the filter that divides the filter into a first and second chamber is permeable to gas prior to the membrane having been wetted with fluid assuming the filter to be a new filter; and if the membrane is permeable to gas concluding that the filter is dry and has been replaced, otherwise concluding that the filter is wet and has not been replaced.

2. The method according to claim 1, further comprising:

isolating a first section of the fluid system including the first chamber of the filter from a second section of the fluid system including the second chamber of the filter;

producing a pressure differential between one of the first and second sections and another of the first and second sections to obtain a higher pressure in the one section, and monitoring the pressure;

opening the other section of the fluid system; and concluding that the filter has been replaced if a drop in the pressure is noted in the one section and that the filter has not been replaced otherwise.

3. The method according to claim 2, further comprising comparing a rate of change of the drop in pressure with a predetermined limit value, and concluding that the filter has been replaced if the rate of change exceeds the limit value.

4. The method according to claim 2, wherein atmospheric air is introduced into one of the first and second sections of the fluid system.

5. The method according to claim 4, wherein the atmospheric air is introduced into the one section of the fluid system through a hydrophobic filter.

6. The method according to claim 1, wherein triggering an optical and/or acoustic alarm in the event the filter has not been replaced by a new filter.

7. A device for extracorporeal treatment of blood, comprising:

at least one filter divided by a membrane into a first chamber and a second chamber, disposed in a fluid system of the device;

means for measuring a gas permeability of the membrane of the at least one filter; and means for determining whether the at least one filter has been replaced or has not been replaced by a corresponding new filter based on the gas permeability of the membrane comprising a verification of whether the membrane has been wetted with fluid.

8. The device according to claim 7, further comprising:

first means for isolating a first section of the fluid system including the first chamber of the filter;

second means for isolating a second section of the fluid system including the second chamber of the filter;

means for supplying a gas to one of the first and second sections for increasing a pressure in the one section; and means for monitoring the pressure in the one section of the fluid system.

9. The device according to claim 8, wherein the means for monitoring the pressure comprise an analyzing unit adapted to compare a rate of decrease of the pressure to a predetermined limit value, and to conclude that the at least one filter has been replaced by the corresponding new filter if the predetermined limit value is exceeded.

10. The device according to claim 8, wherein the means for supplying a gas is an air pump that draws atmospheric air.

11. The device according to claim 10, wherein the air pump draws atmospheric air through an hydrophobic filter.

12. The device according to claim 7, further comprising an optical and/or acoustic alarm to indicate that the at least one filter has not been replaced by the corresponding new filter.

13. A device for extracorporeal treatment of blood, comprising:

a filter divided by a membrane into a first and a second chamber;

a device for introducing or withdrawing gas from one side of the membrane;

an analyzing unit constructed and arranged to compare a change in pressure in the filter with a predetermined value; and an indicator to indicate if the change in pressure exceeds the predetermined value and determine whether the filter is dry the analyzing unit triggering at least one of an alarm or a control action upon a determination that the filter is not dry.

* * * * *